United States Patent
Lomicka et al.

(10) Patent No.: US 8,851,891 B2
(45) Date of Patent: Oct. 7, 2014

(54) EXPANDABLE BONE IMPLANT

(75) Inventors: Matthew Lomicka, Vista, CA (US); Srilakshmi Vishnubhotla, San Diego, CA (US); Jeffrey A. Bassett, Vista, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 11 days.

(21) Appl. No.: 13/314,869

(22) Filed: Dec. 8, 2011

(65) Prior Publication Data
US 2012/0129132 A1    May 24, 2012

Related U.S. Application Data

(62) Division of application No. 12/266,318, filed on Nov. 6, 2008, now abandoned.

(51) Int. Cl.
*A61C 8/00* (2006.01)

(52) U.S. Cl.
CPC .................................. *A61C 8/0033* (2013.01)
USPC ....................................................... 433/173

(58) Field of Classification Search
USPC ................................. 433/172–176
See application file for complete search history.

(56) References Cited

U.S. PATENT DOCUMENTS

| | | | |
|---|---|---|---|
| 2,721,387 A | 10/1955 | Ashuckian | |
| 3,314,420 A | 4/1967 | Smith et al. | |
| 3,423,830 A | 1/1969 | Halpern et al. | |
| 3,423,831 A | 1/1969 | Semmelman | |
| 3,435,526 A | 4/1969 | Brancato | |
| 3,497,953 A | 3/1970 | Weissman | |
| 3,685,115 A | 8/1972 | Scott | |
| 3,713,860 A | 1/1973 | Auskern | |
| 3,740,851 A | 6/1973 | Weissman | |
| 3,797,113 A | 3/1974 | Brainin | |
| 3,849,887 A | 11/1974 | Brainin | |
| 3,896,547 A | 7/1975 | Kulwiec | |

(Continued)

FOREIGN PATENT DOCUMENTS

| CA | 2506854 A1 | 7/2004 |
|---|---|---|
| DE | 4209569 A1 | 11/1994 |

(Continued)

OTHER PUBLICATIONS

"U.S. Appl. No. 12/266,318, Final Office Action mailed Aug. 9, 2011", 10 pgs.

(Continued)

*Primary Examiner* — Sunil K Singh
(74) *Attorney, Agent, or Firm* — Schwegman Lundberg & Woessner, P.A.

(57) ABSTRACT

An expendable bone implant has a first member with a coronal end portion configured for supporting a prosthesis. A second member is at least partially porous, engages the first member, and is configured to expand outwardly upon a longitudinal force being applied to at least one of the first and second members. This anchors the implant in bone before mastication forces are applied to the implant.

27 Claims, 3 Drawing Sheets

(56) References Cited

U.S. PATENT DOCUMENTS

| | | | |
|---|---|---|---|
| 3,905,109 A | 9/1975 | Cohen et al. | |
| 3,906,550 A | 9/1975 | Rostoker et al. | |
| 3,919,773 A | 11/1975 | Freeman | |
| 3,934,347 A | 1/1976 | Lash et al. | |
| 3,992,725 A | 11/1976 | Homsy | |
| 4,011,602 A * | 3/1977 | Rybicki et al. | 623/23.76 |
| 4,016,651 A | 4/1977 | Kawahara et al. | |
| 4,086,701 A | 5/1978 | Kawahara et al. | |
| 4,097,935 A | 7/1978 | Jarcho | |
| 4,122,605 A | 10/1978 | Hirabayashi et al. | |
| 4,131,597 A | 12/1978 | Bluethgen et al. | |
| 4,178,686 A | 12/1979 | Riess et al. | |
| 4,195,366 A | 4/1980 | Jarcho et al. | |
| 4,199,864 A | 4/1980 | Ashman | |
| 4,229,170 A | 10/1980 | Perez | |
| 4,244,689 A | 1/1981 | Ashman | |
| 4,252,525 A | 2/1981 | Child | |
| 4,259,072 A | 3/1981 | Hirabayashi et al. | |
| 4,281,991 A | 8/1981 | Michi et al. | |
| 4,321,042 A | 3/1982 | Scheicher | |
| 4,375,967 A | 3/1983 | Schaefer | |
| 4,379,694 A | 4/1983 | Riess | |
| 4,381,918 A | 5/1983 | Ehrnford | |
| 4,411,624 A | 10/1983 | Ogino et al. | |
| 4,431,420 A | 2/1984 | Adair | |
| 4,439,152 A | 3/1984 | Small | |
| 4,448,758 A | 5/1984 | Nagai et al. | |
| 4,475,892 A | 10/1984 | Faunce | |
| 4,478,904 A | 10/1984 | Ducheyne et al. | |
| 4,483,678 A | 11/1984 | Nishio et al. | |
| 4,484,570 A | 11/1984 | Sutter et al. | |
| 4,492,577 A | 1/1985 | Farris et al. | |
| 4,531,915 A | 7/1985 | Tatum, Jr. | |
| 4,531,916 A | 7/1985 | Scantlebury et al. | |
| 4,536,158 A | 8/1985 | Bruins et al. | |
| 4,548,959 A | 10/1985 | Nagai et al. | |
| 4,556,534 A | 12/1985 | Burnett et al. | |
| 4,708,652 A | 11/1987 | Fujiu et al. | |
| 4,713,006 A | 12/1987 | Hakamatsuka et al. | |
| 4,722,688 A | 2/1988 | Lonca | |
| 4,731,085 A | 3/1988 | Koch | |
| 4,737,411 A | 4/1988 | Graves et al. | |
| 4,743,260 A | 5/1988 | Burton | |
| 4,744,757 A | 5/1988 | Adair et al. | |
| 4,744,759 A | 5/1988 | Bowen | |
| 4,820,157 A | 4/1989 | Salvo | |
| 4,842,517 A | 6/1989 | Kawahara et al. | |
| 4,871,384 A | 10/1989 | Kasuga | |
| 4,872,839 A | 10/1989 | Branjnovic | |
| 4,872,840 A | 10/1989 | Bori | |
| 4,877,400 A | 10/1989 | Holsclaw | |
| 4,880,610 A | 11/1989 | Constantz | |
| 4,906,190 A | 3/1990 | Michna | |
| 4,909,738 A | 3/1990 | Ai et al. | |
| 4,957,554 A | 9/1990 | Mathers et al. | |
| 4,957,819 A | 9/1990 | Kawahara et al. | |
| 4,960,733 A | 10/1990 | Kasuga et al. | |
| 4,969,817 A | 11/1990 | Hiranuma et al. | |
| 4,969,913 A | 11/1990 | Ojima | |
| 4,983,182 A | 1/1991 | Kijima et al. | |
| 5,000,685 A | 3/1991 | Brajnovic | |
| 5,002,488 A | 3/1991 | Homsy | |
| 5,004,421 A | 4/1991 | Lazarof | |
| 5,007,835 A | 4/1991 | Valen | |
| 5,009,709 A | 4/1991 | Ibsen et al. | |
| 5,049,074 A * | 9/1991 | Otani et al. | 433/173 |
| 5,055,497 A | 10/1991 | Okada et al. | |
| 5,061,285 A | 10/1991 | Koch | |
| 5,062,798 A | 11/1991 | Tsuge et al. | |
| 5,064,731 A | 11/1991 | Miyazaki et al. | |
| 5,076,789 A | 12/1991 | Tanaka | |
| 5,087,200 A | 2/1992 | Branjovic et al. | |
| 5,120,340 A | 6/1992 | Ducheyne et al. | |
| 5,123,844 A | 6/1992 | Wakai et al. | |
| 5,125,839 A | 6/1992 | Ingber et al. | |
| 5,125,971 A | 6/1992 | Nonami et al. | |
| 5,139,424 A | 8/1992 | Yli-Urpo | |
| 5,152,687 A | 10/1992 | Amino | |
| 5,176,747 A | 1/1993 | Panzera et al. | |
| 5,180,303 A | 1/1993 | Hornburg et al. | |
| 5,186,626 A | 2/1993 | Tanaka | |
| 5,192,325 A | 3/1993 | Kijima et al. | |
| 5,194,000 A | 3/1993 | Dury | |
| 5,194,001 A | 3/1993 | Salvo | |
| 5,199,873 A | 4/1993 | Schulte et al. | |
| 5,205,745 A | 4/1993 | Kamiya et al. | |
| 5,232,365 A | 8/1993 | Ikehara | |
| 5,232,878 A | 8/1993 | Kasuga et al. | |
| 5,236,458 A | 8/1993 | Ducheyne et al. | |
| 5,238,405 A | 8/1993 | Marlin | |
| 5,254,005 A | 10/1993 | Zuest | |
| 5,282,861 A | 2/1994 | Kaplan | |
| 5,282,863 A | 2/1994 | Burton | |
| 5,288,232 A | 2/1994 | Panzera et al. | |
| 5,306,673 A | 4/1994 | Hermansson et al. | |
| 5,308,391 A | 5/1994 | Komma et al. | |
| 5,310,343 A | 5/1994 | Hasegawa et al. | |
| 5,312,254 A | 5/1994 | Rosenlicht | |
| 5,314,334 A | 5/1994 | Panzera et al. | |
| 5,342,201 A | 8/1994 | Oden | |
| 5,344,318 A | 9/1994 | Wilson et al. | |
| 5,344,457 A | 9/1994 | Pilliar et al. | |
| 5,346,397 A | 9/1994 | Braiman | |
| 5,415,546 A | 5/1995 | Cox, Sr. | |
| 5,419,702 A | 5/1995 | Beaty et al. | |
| 5,425,640 A | 6/1995 | Scharf | |
| 5,439,380 A | 8/1995 | Marlin | |
| 5,443,515 A | 8/1995 | Cohen et al. | |
| 5,449,291 A | 9/1995 | Lueschen et al. | |
| 5,458,488 A | 10/1995 | Chalifoux | |
| 5,468,544 A | 11/1995 | Marcolongo et al. | |
| 5,470,230 A | 11/1995 | Daftary et al. | |
| 5,476,383 A | 12/1995 | Beaty et al. | |
| 5,549,123 A | 8/1996 | Okuyama et al. | |
| 5,554,665 A | 9/1996 | Tateosian et al. | |
| 5,562,733 A | 10/1996 | Weissbach et al. | |
| 5,571,016 A | 11/1996 | Ingber et al. | |
| 5,572,652 A | 11/1996 | Robusto et al. | |
| 5,575,652 A | 11/1996 | Gaffar et al. | |
| 5,584,693 A | 12/1996 | Nishihara | |
| 5,591,030 A | 1/1997 | Thiel et al. | |
| 5,612,049 A | 3/1997 | Li et al. | |
| 5,614,330 A | 3/1997 | Panzera et al. | |
| 5,621,035 A | 4/1997 | Lyles et al. | |
| 5,624,262 A | 4/1997 | Yarovesky et al. | |
| 5,645,934 A | 7/1997 | Marcolongo et al. | |
| 5,674,069 A | 10/1997 | Osorio | |
| 5,676,745 A | 10/1997 | Kelly et al. | |
| 5,683,249 A | 11/1997 | Ibsen et al. | |
| 5,685,714 A | 11/1997 | Beaty et al. | |
| 5,695,337 A | 12/1997 | Tyszblat Sadoun | |
| 5,697,785 A | 12/1997 | Delahaye | |
| 5,697,976 A | 12/1997 | Chesterfield et al. | |
| 5,697,997 A | 12/1997 | Aronsson et al. | |
| 5,698,019 A | 12/1997 | Frank et al. | |
| 5,713,994 A | 2/1998 | Kramer et al. | |
| 5,723,007 A | 3/1998 | Engel et al. | |
| 5,727,943 A | 3/1998 | Beaty et al. | |
| 5,755,809 A | 5/1998 | Cohen et al. | |
| 5,759,036 A | 6/1998 | Hinds | |
| 5,762,500 A | 6/1998 | Lazarof | |
| 5,772,438 A | 6/1998 | Deom | |
| 5,775,912 A | 7/1998 | Panzera et al. | |
| 5,785,524 A | 7/1998 | Wolf | |
| 5,833,463 A | 11/1998 | Hurson | |
| 5,833,464 A | 11/1998 | Foser | |
| 5,839,900 A | 11/1998 | Billet et al. | |
| 5,843,348 A | 12/1998 | Giordano | |
| 5,849,068 A | 12/1998 | Hofmann, geb. Roth et al. | |
| 5,873,721 A | 2/1999 | Willoughby | |
| 5,910,273 A | 6/1999 | Thiel et al. | |
| 5,915,967 A | 6/1999 | Clokie | |
| 5,925,180 A | 7/1999 | Frank et al. | |
| 5,931,674 A | 8/1999 | Hanosh et al. | |

(56) References Cited

U.S. PATENT DOCUMENTS

| | | |
|---|---|---|
| 5,934,906 A | 8/1999 | Phimmasone |
| 5,939,211 A | 8/1999 | Mormann |
| 5,947,732 A | 9/1999 | Beaty et al. |
| 5,947,737 A | 9/1999 | Billet et al. |
| 5,951,290 A | 9/1999 | Ardizio et al. |
| 5,951,293 A | 9/1999 | Billet et al. |
| 5,951,295 A | 9/1999 | Lyles et al. |
| 5,964,592 A | 10/1999 | Hites et al. |
| 5,971,760 A | 10/1999 | Letcher |
| 5,975,905 A | 11/1999 | Kim et al. |
| 5,984,683 A | 11/1999 | Sakata et al. |
| 5,989,026 A | 11/1999 | Rogers et al. |
| 5,989,027 A | 11/1999 | Wagner et al. |
| 6,010,337 A | 1/2000 | Billet et al. |
| 6,012,923 A | 1/2000 | Bassett et al. |
| 6,013,591 A | 1/2000 | Ying et al. |
| 6,027,742 A | 2/2000 | Lee et al. |
| 6,039,568 A | 3/2000 | Hinds |
| 6,045,361 A | 4/2000 | Misch et al. |
| 6,048,203 A | 4/2000 | Rosenberg |
| 6,048,205 A | 4/2000 | Wright |
| 6,054,400 A | 4/2000 | Brink et al. |
| RE36,689 E | 5/2000 | Beaty et al. |
| 6,056,547 A | 5/2000 | Names |
| 6,063,442 A | 5/2000 | Cohen et al. |
| 6,080,692 A | 6/2000 | Reise et al. |
| 6,087,553 A | 7/2000 | Cohen et al. |
| 6,117,456 A | 9/2000 | Lee et al. |
| 6,120,293 A | 9/2000 | Lazzara et al. |
| 6,126,445 A | 10/2000 | Willoughby |
| 6,126,732 A | 10/2000 | Hofmann et al. |
| 6,135,775 A | 10/2000 | Weisman |
| 6,146,423 A | 11/2000 | Cohen et al. |
| 6,152,737 A | 11/2000 | Beaty et al. |
| 6,159,010 A | 12/2000 | Rogers et al. |
| 6,159,417 A | 12/2000 | Giordano |
| 6,168,435 B1 | 1/2001 | Beaty et al. |
| 6,168,436 B1 | 1/2001 | O'Brien |
| 6,168,633 B1 | 1/2001 | Shoher et al. |
| 6,183,256 B1 | 2/2001 | Fisher et al. |
| 6,183,515 B1 | 2/2001 | Barlow et al. |
| 6,186,791 B1 | 2/2001 | Karmaker et al. |
| 6,193,516 B1 | 2/2001 | Story |
| 6,200,137 B1 | 3/2001 | Holand et al. |
| 6,206,192 B1 | 3/2001 | Winstead et al. |
| 6,213,775 B1 | 4/2001 | Reipur |
| 6,214,368 B1 | 4/2001 | Lee et al. |
| 6,224,662 B1 | 5/2001 | Nemeth |
| 6,227,860 B1 * | 5/2001 | Hobo ..................... 433/173 |
| 6,244,869 B1 | 6/2001 | Billet et al. |
| 6,250,922 B1 | 6/2001 | Bassett et al. |
| 6,267,597 B1 | 7/2001 | Kim |
| 6,270,347 B1 | 8/2001 | Webster et al. |
| 6,271,282 B1 | 8/2001 | Giordano |
| 6,280,863 B1 | 8/2001 | Frank et al. |
| 6,283,753 B1 | 9/2001 | Willoughby |
| 6,287,341 B1 | 9/2001 | Lee et al. |
| 6,299,448 B1 | 10/2001 | Zdrahala et al. |
| 6,306,784 B1 | 10/2001 | Drescher et al. |
| 6,322,728 B1 | 11/2001 | Brodkin et al. |
| 6,325,628 B1 | 12/2001 | Morgan |
| 6,331,312 B1 | 12/2001 | Lee et al. |
| 6,342,202 B1 | 1/2002 | Steidl et al. |
| 6,342,458 B1 | 1/2002 | Schweiger et al. |
| 6,343,930 B1 | 2/2002 | Beaty et al. |
| 6,345,984 B2 | 2/2002 | Karmaker et al. |
| 6,354,836 B1 | 3/2002 | Panzera et al. |
| 6,362,250 B1 | 3/2002 | Karmaker et al. |
| 6,362,251 B1 | 3/2002 | Alkemper et al. |
| 6,379,153 B1 | 4/2002 | Schroering |
| 6,386,876 B1 | 5/2002 | Lee |
| 6,394,806 B1 | 5/2002 | Kumar |
| 6,402,517 B1 | 6/2002 | Hozumi et al. |
| 6,419,491 B1 | 7/2002 | Ricci et al. |
| 6,431,868 B2 | 8/2002 | Story |
| 6,439,890 B1 | 8/2002 | Karmaker et al. |
| 6,447,549 B1 | 9/2002 | Taft |
| 6,450,813 B1 | 9/2002 | McDonald et al. |
| 6,451,292 B2 | 9/2002 | Warford, III et al. |
| 6,454,569 B1 | 9/2002 | Hollander et al. |
| 6,485,849 B2 | 11/2002 | Petticrew |
| 6,495,073 B2 | 12/2002 | Bodenmiller et al. |
| 6,497,573 B2 | 12/2002 | Wagner et al. |
| 6,503,625 B1 | 1/2003 | Rieder et al. |
| 6,514,453 B2 | 2/2003 | Vigliotti et al. |
| 6,527,553 B2 | 3/2003 | Yeung |
| 6,540,784 B2 | 4/2003 | Barlow et al. |
| 6,627,327 B2 | 9/2003 | Reidt et al. |
| 6,641,775 B2 | 11/2003 | Vigliotti et al. |
| 6,648,645 B1 | 11/2003 | MacDougald et al. |
| 6,666,684 B1 | 12/2003 | Names |
| 6,669,476 B2 | 12/2003 | Prestipino et al. |
| 6,679,701 B1 | 1/2004 | Blacklock |
| 6,689,202 B2 | 2/2004 | Panzera |
| 6,743,936 B1 | 6/2004 | Wellinhoff et al. |
| 6,752,863 B2 | 6/2004 | Lyles et al. |
| 6,755,651 B2 | 6/2004 | Brodbeck |
| 6,787,584 B2 | 9/2004 | Jia et al. |
| 6,797,006 B2 | 9/2004 | Hodorek |
| 6,808,659 B2 | 10/2004 | Schulman et al. |
| 6,821,462 B2 | 11/2004 | Schulman et al. |
| 6,846,181 B2 | 1/2005 | Karmaker et al. |
| 6,878,456 B2 | 4/2005 | Castro et al. |
| 6,881,488 B2 | 4/2005 | Giordano |
| 6,916,177 B2 | 7/2005 | Lin et al. |
| 6,932,606 B2 | 8/2005 | Aravena et al. |
| 6,945,448 B2 | 9/2005 | Medlin et al. |
| 6,949,251 B2 | 9/2005 | Dalal et al. |
| 6,953,594 B2 | 10/2005 | Lee et al. |
| 6,976,999 B2 | 12/2005 | Charlebois et al. |
| 6,984,261 B2 | 1/2006 | Cummings et al. |
| 6,986,660 B2 | 1/2006 | Kumar et al. |
| 6,994,726 B2 | 2/2006 | Lin et al. |
| 7,011,522 B2 | 3/2006 | Panzera et al. |
| 7,291,012 B2 | 11/2007 | Lyren |
| 8,231,387 B2 * | 7/2012 | Salvi et al. ............ 433/174 |
| 2001/0000486 A1 | 4/2001 | Story |
| 2001/0051832 A1 | 12/2001 | Bakker et al. |
| 2002/0028424 A1 | 3/2002 | Prestipino et al. |
| 2002/0039718 A1 | 4/2002 | Kwan |
| 2002/0076673 A1 | 6/2002 | Wagner et al. |
| 2002/0095123 A1 | 7/2002 | Smutney et al. |
| 2002/0115742 A1 | 8/2002 | Trieu et al. |
| 2002/0155412 A1 | 10/2002 | Panzera et al. |
| 2002/0160334 A1 | 10/2002 | Brodbeck |
| 2003/0031984 A1 | 2/2003 | Rusin et al. |
| 2003/0068598 A1 | 4/2003 | Vallittu et al. |
| 2003/0073394 A1 | 4/2003 | Reidt et al. |
| 2003/0087984 A1 | 5/2003 | Erbe et al. |
| 2003/0096214 A1 | 5/2003 | Luthardt et al. |
| 2003/0134925 A1 | 7/2003 | Guzauskas |
| 2003/0148247 A1 | 8/2003 | Sicurelli, Jr. et al. |
| 2004/0024081 A1 | 2/2004 | Trieu et al. |
| 2004/0058299 A1 | 3/2004 | Molin et al. |
| 2004/0064192 A1 | 4/2004 | Bubb |
| 2004/0097627 A1 | 5/2004 | Vallittu et al. |
| 2004/0106085 A1 | 6/2004 | Vallittu et al. |
| 2004/0106087 A1 | 6/2004 | Weigl et al. |
| 2004/0131562 A1 | 7/2004 | Gower et al. |
| 2004/0152034 A1 | 8/2004 | Cummings et al. |
| 2004/0170946 A1 | 9/2004 | Lyren |
| 2004/0197737 A1 | 10/2004 | Uckelmann et al. |
| 2004/0234925 A1 | 11/2004 | Benhamou |
| 2004/0241614 A1 | 12/2004 | Goldberg et al. |
| 2005/0014108 A1 | 1/2005 | Wohrle et al. |
| 2005/0023710 A1 | 2/2005 | Brodkin et al. |
| 2005/0028424 A1 | 2/2005 | Poinski |
| 2005/0031704 A1 | 2/2005 | Ahn |
| 2005/0084533 A1 | 4/2005 | Howdle et al. |
| 2005/0084819 A1 | 4/2005 | Sims et al. |
| 2005/0084821 A1 | 4/2005 | Sims et al. |
| 2005/0096652 A1 | 5/2005 | Burton |
| 2005/0100724 A1 | 5/2005 | Seargeant |
| 2005/0109060 A1 | 5/2005 | Cummings et al. |

(56) References Cited

U.S. PATENT DOCUMENTS

| | | |
|---|---|---|
| 2005/0123672 A1 | 6/2005 | Justin et al. |
| 2005/0184134 A1 | 8/2005 | Charlebois et al. |
| 2005/0191248 A1 | 9/2005 | Hunter et al. |
| 2005/0221259 A1 | 10/2005 | Anderson |
| 2005/0261795 A1 | 11/2005 | Ghosh et al. |
| 2005/0266382 A1 | 12/2005 | Soler et al. |
| 2006/0075826 A1 | 4/2006 | Roberts et al. |
| 2007/0015110 A1 | 1/2007 | Zhang et al. |
| 2007/0111165 A1 | 5/2007 | Wallick et al. |
| 2007/0118221 A1 | 5/2007 | Robie et al. |
| 2007/0148321 A1 | 6/2007 | Yakir et al. |
| 2007/0184265 A1 | 8/2007 | Ranganathan et al. |
| 2008/0050699 A1 | 2/2008 | Zhang et al. |
| 2008/0241793 A1 | 10/2008 | Collins et al. |
| 2009/0011384 A1 | 1/2009 | Collins et al. |
| 2009/0036908 A1 | 2/2009 | Zokol et al. |
| 2009/0061387 A1 | 3/2009 | Lomicka et al. |
| 2009/0061388 A1 | 3/2009 | Collins et al. |
| 2009/0061389 A1 | 3/2009 | Lomicka et al. |
| 2009/0098510 A1 | 4/2009 | Zhang |
| 2009/0098511 A1 | 4/2009 | Zhang |
| 2009/0215007 A1 | 8/2009 | Caterini et al. |
| 2010/0003638 A1 | 1/2010 | Collins et al. |
| 2010/0003639 A1 | 1/2010 | Salvi et al. |
| 2010/0003640 A1 | 1/2010 | Damstra et al. |

FOREIGN PATENT DOCUMENTS

| | | |
|---|---|---|
| DE | 19529036 A1 | 3/1997 |
| DE | 10105398 A1 | 8/2002 |
| EP | 0266313 A2 | 5/1988 |
| EP | 0271236 A1 | 6/1988 |
| EP | 0345581 A2 | 12/1989 |
| EP | 0366018 A1 | 5/1990 |
| EP | 0417018 A1 | 3/1991 |
| EP | 0467948 A1 | 1/1992 |
| EP | 0498923 A1 | 8/1992 |
| EP | 0333503 A2 | 2/1993 |
| EP | 0560279 A1 | 9/1993 |
| EP | 0806211 A1 | 11/1997 |
| EP | 0950421 A1 | 10/1999 |
| EP | 1281372 A1 | 2/2003 |
| EP | 1598028 A1 | 11/2005 |
| EP | 1712205 A2 | 10/2006 |
| FR | 2796265 A1 | 1/2001 |
| GB | 1526780 A | 9/1978 |
| GB | 2401867 A | 11/2004 |
| GB | 2416996 A1 | 2/2006 |
| JP | 61275205 A | 12/1986 |
| JP | 63290559 A | 11/1988 |
| JP | 1025849 A | 1/1989 |
| JP | 2002126071 A | 5/2002 |
| WO | WO-8900410 A1 | 1/1989 |
| WO | WO-9011979 A1 | 10/1990 |
| WO | WO-9320773 A1 | 10/1993 |
| WO | WO-9421190 A1 | 9/1994 |
| WO | WO-9528973 A1 | 11/1995 |
| WO | WO-9721393 A1 | 6/1997 |
| WO | WO-9741809 A1 | 11/1997 |
| WO | WO-9830170 A1 | 7/1998 |
| WO | WO-0021455 A1 | 4/2000 |
| WO | WO-0132072 A2 | 5/2001 |
| WO | WO-0187193 A1 | 11/2001 |
| WO | WO-0234155 A1 | 5/2002 |
| WO | WO-0236039 A1 | 5/2002 |
| WO | WO-02062901 A1 | 8/2002 |
| WO | WO-02064100 A1 | 8/2002 |
| WO | WO-03065939 A1 | 8/2003 |
| WO | WO-03065996 A2 | 8/2003 |
| WO | WO-03078508 A1 | 9/2003 |
| WO | WO-03094774 A1 | 11/2003 |
| WO | WO-2004054464 A2 | 7/2004 |
| WO | WO-2006082610 A2 | 8/2006 |
| WO | WO-2007027794 A1 | 3/2007 |
| WO | WO-2007086832 A2 | 8/2007 |
| WO | WO-2010053767 A1 | 5/2010 |

OTHER PUBLICATIONS

"U.S. Appl. No. 12/266,318, Non Final Office Action mailed Feb. 23, 2011", 9 pgs.

"U.S. Appl. No. 12/266,318, Response filed Feb. 4, 2011 to Restriction Requirement mailed Jan. 4, 2011", 7 pgs.

"U.S. Appl. No. 12/266,318, Response filed May 27, 2011 to Non Final Office Action mailed Feb. 23, 2011", 12 pgs.

"U.S. Appl. No. 12/266,318, Response filed Oct. 7, 2010 to Restriction Requirement mailed Sep. 14, 2010", 7 pgs.

"U.S. Appl. No. 12/266,318, Restriction Requirement mailed Jan. 4, 2011", 6 pgs.

"U.S. Appl. No. 12/266,318, Restriction Requirement mailed Sep. 14, 2010", 6 pgs.

"European Application Serial No. 09744565.4, Office Action mailed May 29, 2012", 5 pgs.

"European Application Serial No. 09744565.4, Office Action mailed Sep. 9, 2011", 2 pgs.

"Flocculants, Binders, and Bonds", Chapter 11, Molecular Binders, (1995), 173-177.

"International Application Serial No. PCT/US2006/020130, International Search Report mailed Feb. 6, 2007", 7 pgs.

"International Application Serial No. PCT/US2006/033893, International Search Report mailed Jan. 29, 2007", 1 pg.

"International Application Serial No. PCT/US2007/069562, International Search Report mailed Jul. 7, 2008", 1 pg.

"International Application Serial No. PCT/US2008/074616, International Search Report mailed Dec. 16, 2008", 4 pgs.

"International Application Serial No. PCT/US2008/074642, International Search Report mailed Feb. 12, 2009", 4 pgs.

"International Application Serial No. PCT/US2008/074645, International Search Report mailed Dec. 29, 2008", 9 pgs.

"International Application Serial No. PCT/US2008/074655, International Search Report mailed Feb. 18, 2009", 9 pgs.

"International Application Serial No. PCT/US2009/048456, International Search Report mailed Apr. 27, 2010", 5 pgs.

"International Application Serial No. PCT/US2009/048469, International Search Report mailed Oct. 19, 2009", 9 pgs.

"International Application Serial No. PCT/US2009/048476, International Search Report mailed Dec. 10, 2009", 13 pgs.

"International Application Serial No. PCT/US2009/048481, International Search Report mailed Dec. 10, 2009", 13 pgs.

"International Application Serial No. PCT/US2009/062308, International Preliminary Report on Patentability mailed May 10, 2011", 8 pgs.

"International Application Serial No. PCT/US2009/062308, International Search Report mailed Jan. 21, 2010", 9 pgs.

"International Application Serial No. PCT/US2009/062308, Written Opinion mailed Jan. 21, 2010", 8 pgs.

"PEEK-CLASSIX", Information Sheet Invibio Ltd., Properties of PEEK-CLASSIX White Granular, (Nov. 2003), 2 pgs.

"The Clinical Assessment of a Ceramic-Coated Transmucosal Dental Implant Collar", International Journal of Prosthodonics vol. 9, Issue 5, (1996), 466-472.

"Two Applications of Transmucosal Milled Ceramic in Implantology", Preliminary Clinical Examples; Implant Quintessence International vol. 27, Issue 8, (1996), 533-548.

Cass, Richard B, et al., "Innovative Ceramic-Fiber Technology Energizes Advanced Cerametrics", The American Ceramic Society, American Ceramic Society Bulletin, (Nov. 2003), 9701-9706.

Ganz, Scott D, "Presurgical Planning With CT-Derived Fabrication of Surgical Guides", J Oral Maxiofac Surg 63, Suppl 2, (2005), 59-73 pgs.

Kan, Joseph Y K, "Computer-Guided Immediate Provisionalization of Anterior Multiple Adjacent Implants: Surgical and Prosthodontic Rationale", Practical Procedures & Aethetic Dentistry, vol. 18, No. 10, (2006), 617-623 pgs.

(56) References Cited

OTHER PUBLICATIONS

Matinlinna, Jukka P, et al., "An Introduction to Silanes and Their Clinical Applications in Dentistry", The International Journal of Prosthodontics, vol. 17, No. 2, (2004), 155-164.

Reed, James S., "Chapter 24, Injection Molding", Principles of Ceramics Processing, 2nd Edition, New York : Wiley, (1995), 477-481.

Rosenfeld, Alan L, "Prosthetically Directed Implant Placement Using Computer Software to Ensure Precise Placement and Predictable Prosthetic Outcomes. Part 1: Diagnostics, Imaging, and Collaborative Accountability", International Journal of Periodontics & Restorative Dentistry, vol. 26, No. 3, (2006), 215-221 pgs.

Zhou, Yan, et al., "Shape Optimization of Randomly Oriented Short Fibers for Bone Cement Reinforcements", Materials Science & Engineering A 393, (2005), 374-381.

"European Application Serial No. 09744565.4, Response filed Dec. 5, 2012 to Examination Notification Art. 94(3) mailed May 29, 2012", 14 pgs.

"European Application Serial No. 09744565.4, Examination Notification Art. 94(3) mailed Oct. 11, 2013", 6 pgs.

European Application Serial No. 09744565.4, Response filed Apr. 15, 2014 to Examination Notification Art. 94(3) mailed Oct. 11, 2013, 9 pgs.

\* cited by examiner

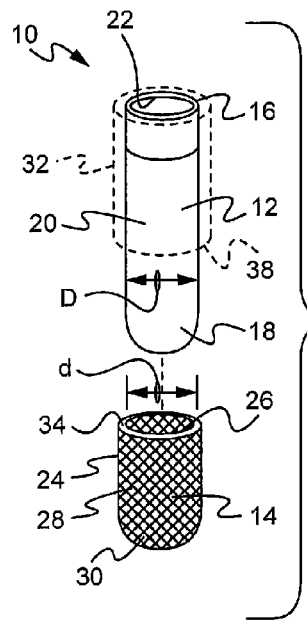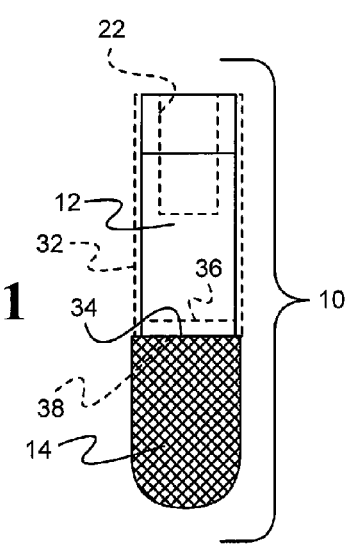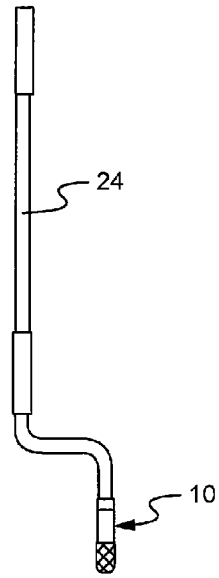
Fig. 1　　Fig. 2　　Fig. 3
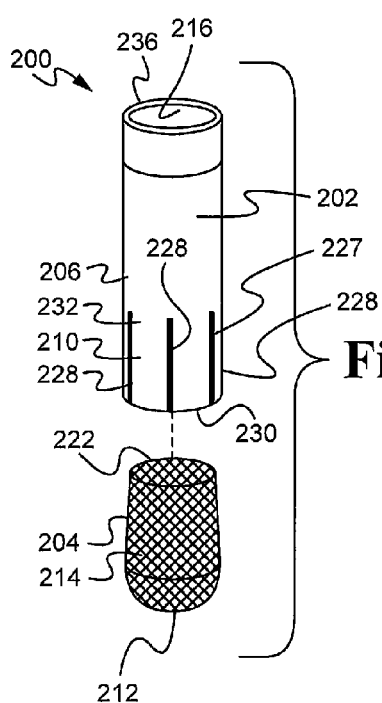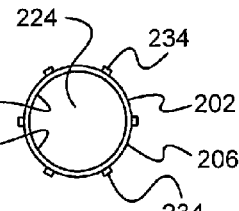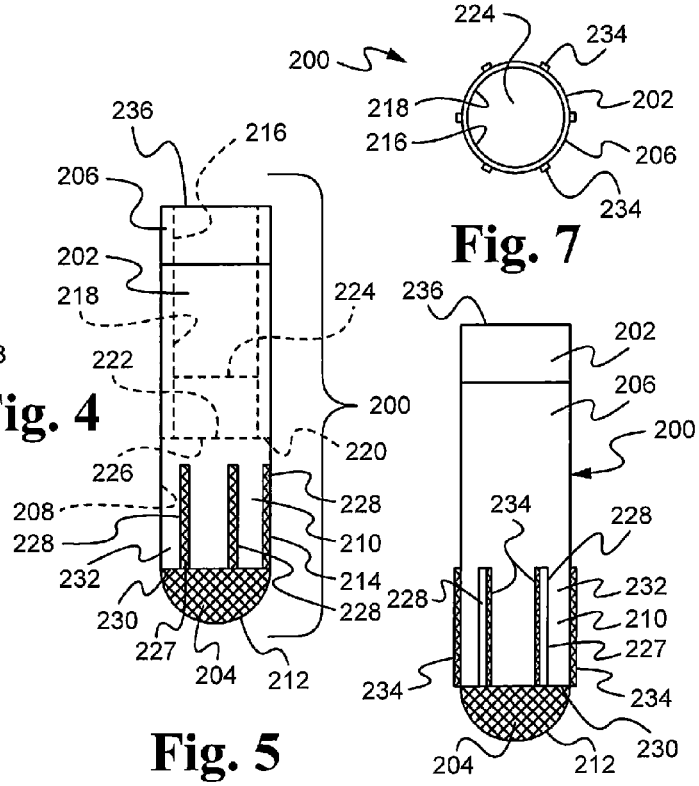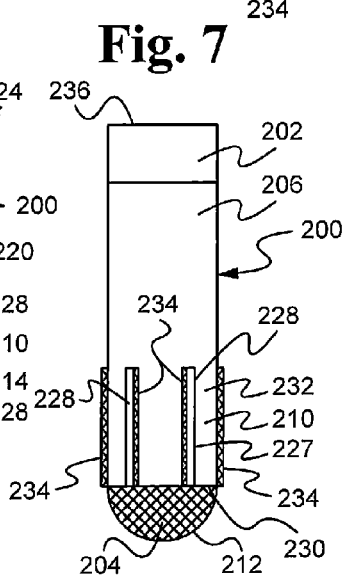
Fig. 4　　Fig. 7　　Fig. 5　　Fig. 6

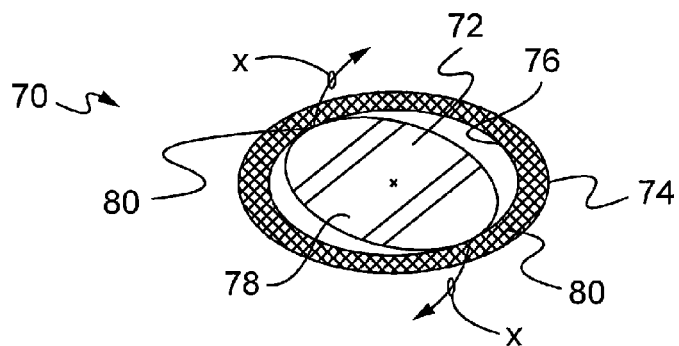
Fig. 8
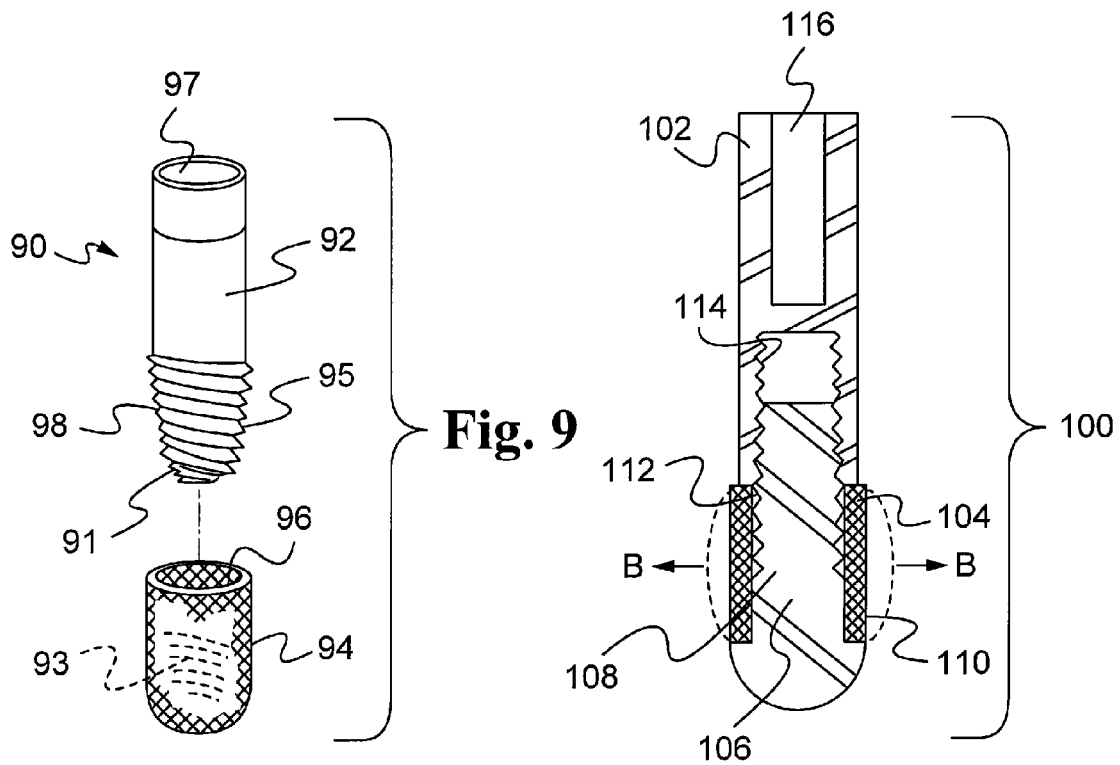
Fig. 9
Fig. 10

EXPANDABLE BONE IMPLANT

CROSS-REFERENCE TO RELATED APPLICATION

This application is a divisional of U.S. patent application Ser. No. 12/266,318, filed on Nov. 6, 2008.

FIELD OF THE INVENTION

The present invention relates to an implant for insertion into bone and, in particular, an expandable bone implant having improved osseointegration features.

BACKGROUND OF THE INVENTION

One type of bone implant is a dental implant or endosseous root form implant which is surgically implanted into a patient's upper or lower jaw to directly or indirectly anchor and support prosthetic devices, such as an artificial tooth. The implants are usually placed at one or more edentulous sites in a patient's dentition at which the patient's original teeth have been lost or damaged in order to restore the patient's chewing function. In many cases, the implant anchors a dental abutment, which in turn provides an interface between the implant and a dental restoration. The restoration is typically a porcelain crown fashioned according to known methods.

The implant is usually either threaded or press-fit into a bore which is drilled into the patient's mandible or maxilla at the edentulous site. The implant is inserted by applying a force to the coronal end of the implant in an insertion direction.

A patient typically prefers to leave after initial surgery with some type of restoration mounted on the implant, which transfers occlusive loads to the implant. Also, it has been shown that in many instances, healing of both soft and hard tissue is improved if the implant is loaded after surgery through a restoration. While the implant rarely receives the full load of occlusion during this healing phase and even with the restoration, the loading is sufficient to displace the implant. Thus, threads are used to achieve initial stability. Before biologic integration has time to take place, the thread resists tension, twisting or bending loads the implant might be subjected to.

The surgical procedure for inserting the threaded implants, however, can be complicated and requires that the threaded implants be turned into place, which further requires the use of special tools and inserts. The torque needed to place the implant into the jaw can be high and may require tapping of the bore on the jaw, which adds yet another step to the surgical procedure where tapping typically is not desired. Also with threaded implants, it is often difficult to achieve optimal esthetics because the geometry of the thread establishes a fixed relationship between the final vertical and rotational orientation of the implant such that a vertical adjustment of the implant requires a rotational adjustment and vice-versa. Thus, a prosthetic held at an ideal rotational orientation by the implant may not have the ideal vertical position.

Alternatively, although a press fit implant has a much simpler surgical procedure, the current press fit designs provide very little initial stability and are not well suited for early and immediate loading procedures that are currently used in dentistry.

The body of the dental implant has commonly been formed of titanium metal or titanium alloys. Titanium metals and alloys may act to enhance bone attachment to the surface of the dental implant. However, the titanium metals and alloys are orders of magnitude higher in stiffness than human bone and as a result absorb much of the mastication forces introduced in the mouth. This absorption of the forces by the titanium dental implants can result in inadequate stimulation of the surrounding bone tissue in the jaw, which over extended periods of time can cause the bone tissue to be resorbed by the body resulting in saucerization of the bone, or bone die-back. Over time, this bone die-back can cause the dental implant to loosen within its hole and even cause infection to the area. Accordingly, a press-fit implant is desired that provides sufficient initial stability while also providing improved osseointegration.

BRIEF DESCRIPTION OF THE DRAWINGS

FIG. 1 is an exploded, side perspective view of a first embodiment of an implant according to the present invention;

FIG. 2 is a side elevational view of the implant of FIG. 1;

FIG. 3 is a side elevational view of an osteotome according to the present invention and having the implant of FIG. 2 attached at its distal end;

FIG. 4 is an exploded, side perspective view of a second embodiment of an implant according to the present invention;

FIG. 5 is a side elevational view of the implant of FIG. 4;

FIG. 6 is a side elevational view of the implant of FIG. 4 showing a porous component expanded through slots in a shell component;

FIG. 7 is a top view of the implant of FIG. 6;

FIG. 8 is an upper, cross-sectional view of a third embodiment of an implant according to the present invention;

FIG. 9 is an exploded, side perspective view of a fourth embodiment of an implant according to the present invention;

FIG. 10 is a side cross-sectional view of a fifth embodiment of an implant according to the present invention;

DETAILED DESCRIPTION

Figure 11:
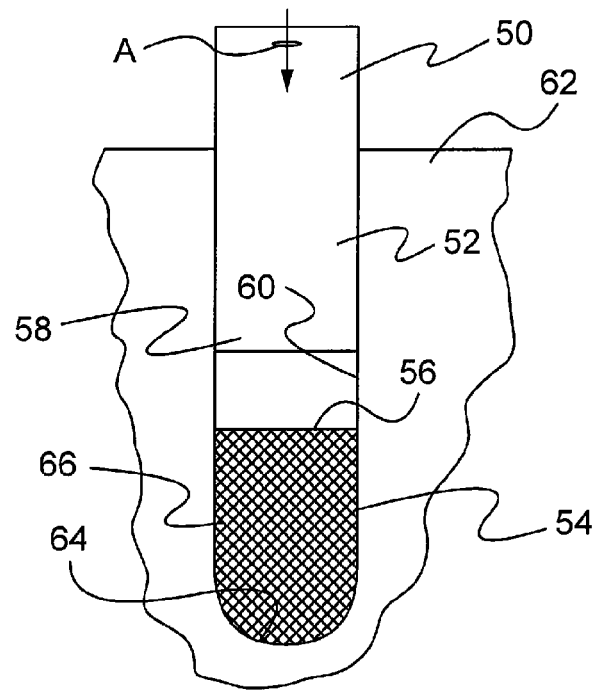
FIG. 11 is a side, exploded view of a sixth embodiment of an implant according to the invention and shown on a bore in bone.

Referring to FIGS. 1-2, an implant 10 is provided for insertion into a surgical site such as a bore on bone, and in the particular examples here, into a mandible or maxilla. The implant 10 is used to support an abutment, and a prosthesis is mounted on the abutment. While two-stage endosseous implants are shown that terminate at the alveolar ridge, it will be understood that the implants may alternatively be single-stage implants with an integrally formed transgingival region or a one-piece implant with an integral abutment.

Implant 10, as well as other implants described herein, are press-fit implants and forego the use of threads as the main mechanism to engage bone. This permits these implants to be placed at a desired depth in bone by using a longitudinal driving force without the need to rotate the implant and while still forming sufficient initial stability to withstand mastication forces.

More specifically, implant 10 has a first, relatively rigid member or component 12, and a second, expandable, porous member or component 14 that is at least partially porous. The rigid member 12 is positioned coronally of the porous member 14 and has a coronal or proximal end portion 16 to directly or indirectly support a prosthesis. The porous member 14 engages an apical or distal end portion 18 of the rigid member 12 when it is placed in a bore in bone. With this structure, a longitudinal force may be applied to the rigid member 12 so that the rigid member 12 impacts against the porous member. This driving force causes the porous member 14 to expand radially outward (and apically) into the surrounding bone of the surgical site. Thus, this expansion occurs before mastication takes place so that the implant 10 is well settled and generally will not expand further during full load mastication.

The rigid member 12 is formed of a relatively strong, hard metal such as titanium. The porous material forming the porous member 14 is particularly suited to form an immediate strong, stable interference fit with surrounding bone while improving osseointegration of the bone into the porous member 14. The porous member 14, in one form is a porous tantalum portion 40 (shown on FIG. 12), which is a highly porous biomaterial useful as a bone substitute and/or cell and tissue receptive material. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is fully incorporated herein by reference. Other metals such as niobium, or alloys of tantalum and niobium with one another or with other metals may also be used.

Figure 12:
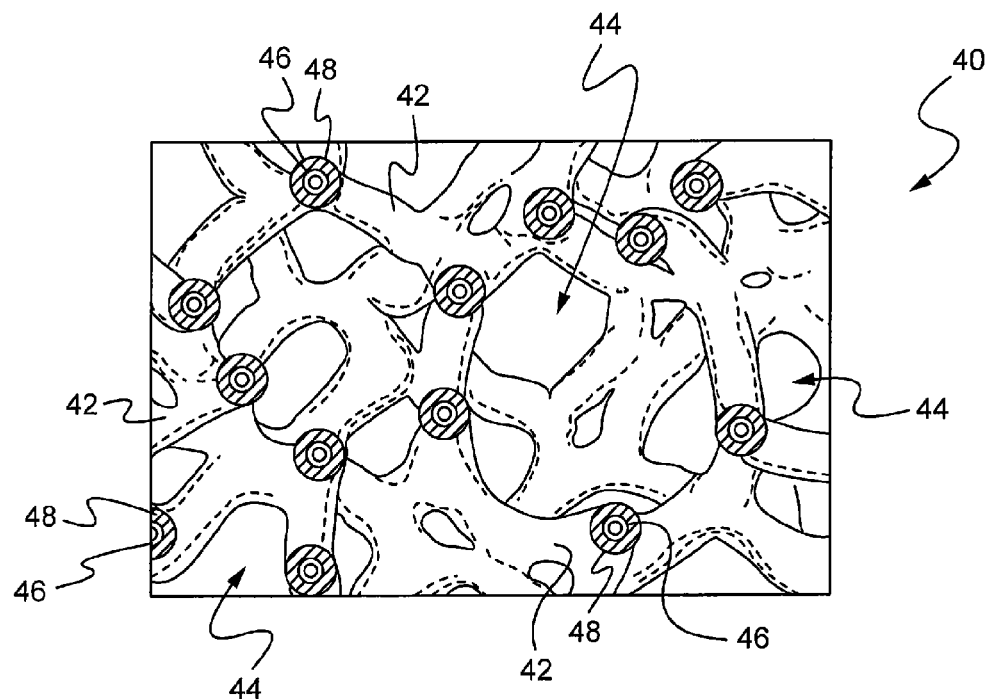
FIG. 12 is an enlarged fragmentary view of a porous tantalum portion for any of the embodiments herein and in accordance with the present invention.

As shown in FIG. 12, porous tantalum structure 40 includes a large plurality of ligaments 42 defining open spaces 44 therebetween, with each ligament 42 generally including a carbon core 46 covered by a thin film of metal 48 such as tantalum, for example. The open spaces 44 between ligaments 42 form a matrix of continuous channels having no dead ends, such that growth of cancellous bone through porous tantalum structure 40 is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to anchor implant 10 into the surrounding bone of a patient's jaw which increases stability. The rough exterior surface of such porous metal portion has a relatively high friction coefficient with adjacent bone forming the bore that receives the implant to further increase initial stability as alluded to above. This structure can produce superior aesthetic results by restricting movement of the implant. These implants can be placed without supplementary surgical procedures, such as bone grafting, and can be placed in areas where traditional implants have been less successful, such as with reduced or decayed alveolar sections.

Porous tantalum structure 40 may be made in a variety of densities in order to selectively tailor the structure for particular applications. In particular, as discussed in the above-incorporated U.S. Pat. No. 5,282,861, the porous tantalum may be fabricated to virtually any desired porosity and pore size, whether uniform or varying, and can thus be matched with the surrounding natural bone in order to provide an improved matrix for bone in-growth and mineralization. This includes a gradation of pore size on a single implant such that pores are larger on an apical end to match cancellous bone and smaller on a coronal end to match cortical bone, or even to receive soft tissue ingrowth. Also, the porous tantalum could be made denser with fewer pores in areas of high mechanical stress. Instead of smaller pores in the tantalum, this can also be accomplished by filling all or some of the pores with a solid material which is described in further detail below.

To provide additional initial mechanical strength and stability to the porous structure 14, the porous structure 14 may be infiltrated with filler material such as a non-resorbable polymer or a resorbable polymer. Examples of non-resorbable polymers for infiltration of the porous structure 14 may include a polyaryl ether ketone (PAEK) such as polyether ketone ketone (PEKK), polyether ether ketone (PEEK), polyether ketone ether ketone ketone (PEKEKK), polymethyl methacrylate (PMMA), polyetherimide, polysulfone, and polyphenolsulfone. Examples of resorbable polymers may include poly lactic acid (PLA), poly glycolic acid (PGA), poly lactic co-glycolic acid (PLGA), polyhydroxybutyrate (PHB), polyhydroxyvalerate (PHV), and copolymers thereof, polycaprolactone, polyanhydrides, and polyorthoesters. The resorbable material would resorb as the bone grows in and replaces it, which maintains the strength and stability of the implant.

Regarding the initial stability, as the porous member 14 is inserted into the bore in bone, the porous material will bite into the bone by grating, chipping and/or flaking bone pieces off of the sidewalls of the bore in which the implant device is being placed. When the implant is press-fit into the bore rather than threaded into the bore, this "rasping" action may form slight recesses or indents within the bore sidewall in which the implant device sits. This restricts rotational or twisting motion of the implant device within the bore since the implant device does not have the clearance to rotate out of the indents and within the bore.

The rasping action also accelerates osseointegration onto the implant device and into the pores of the porous material due to the bone compaction into the pores. First, the grating of the bone structure causes the bone to bleed which stimulates bone growth by instigating production of beneficial cells such as osteoblasts and osteoclasts. Second, the bone pieces that fall into the pores on the porous material assist with bone remodeling. In the process of bone remodeling, osteoblast cells use the bone pieces as scaffolding and create new bone material around the bone pieces. Meanwhile osteoclast cells remove the bone pieces through resorption by breaking down bone and releasing minerals, such as calcium, from the bone pieces and back into the blood stream. The osteoblast cells will continue to replace the grated bone pieces from the pores and around the implant device with new and healthy bone within and surrounding the extraction site. The composite of in-grown bone and porous tantalum has elastic properties much closer to bone than a solid metal implant, creating a loading environment that is conducive to maintaining bone near the implant. Thus, with the porous material, the porous member 14, and in turn the implant 10, has increased resistance to twisting or rotation, allows for immediate or very early loading, and increases long-term stability due to the improved osseointegration. Such an implant with ingrown bone has stability greater than a comparably sized implant with only on-grown bone.

The properties of the porous material also enable expansion of the porous member 14 to anchor the porous member 14 into the surrounding bone. To expand the porous material for any of the implants described herein, the modulus of elasticity (i.e., the amount of deformation in the elastic region of the stress/strain curve when a given stress is applied) of the porous material, or at least that portion of the porous member that will expand, should be about 3 Gpa or less.

As the porous material of any of the implants described herein expands radially against the bone, the porous material cuts into the bone. This occurs because the outer surface of the porous material can be made to have trabeculi or sharp protrusions of metal that extend from the outer surface. These trabeculi are formed when a "cell" of the porous tantalum is cut leaving only a portion of each strut that make up a porous tantalum "cell." It is believed that the trabeculi, when compressed against the bone surface, cut into the bone because the porous tantalum metal can withstand greater stress than many types of bone tissue. The result of this digging in or rasping action with the cut struts further increases the initial stability of the implant in the surgical site in addition to the uncut struts described above.

To provide this cutting action as the porous member for any of the implants described herein expands, the compressive strength of the porous metal should be from about 50 to about 90 MPa, which is relatively higher than the compressive strength of cancellous bone which is about 10 to about 50 MPa. The area of contact between each trabeculi and the bone will be very small due to the geometry of the trabeculi as described above. This will result in high stress (load/area) when even moderate loads are applied. Since the amount of stress the porous tantalum metal can achieve prior to yield is higher than the surrounding bone tissue, the porous material will dig into the bone.

Referring again to FIGS. 1-2, in one form, the rigid member 12 is generally bullet-shaped with a cylindrical outer surface 20 that terminates in the apical end portion 18 which is rounded. The outer surface 20 can be smooth but may be roughened or otherwise treated to promote bone growth or restrict bacterial growth. The coronal end portion 16 of the rigid member 12 is open to an inner longitudinal cavity 22 for receiving a driving device such as an osteotome 24 (shown in FIG. 3) and/or for receiving fasteners to secure an abutment to the implant 10. The longitudinal cavity 22 may have a circular cross-section for the purpose of receiving a longitudinal force from the driving tool. The longitudinal cavity 22, however, may also have a non-circular cross-section, or have a non-circular portion, such as polygonal, to receive an abutment, a fastener holding an abutment, or to limit rotation of the driving tool relative to the implant 10 for convenience while inserting the implant 10 in the bore.

The porous member 14 is generally cup-shaped and forms a coronally accessible, longitudinally extending, interior cavity 26. The porous member 14 has a generally cylindrical wall 28 as well as a rounded apical end portion 30 that cooperatively defines the cavity 26. The apical end portion 30 has a shape that corresponds to the shape of apical end portion 18. To facilitate expansion, the wall 28 should not be too thick, and in one aspect, has a thickness from about 0.020 inches to about 0.040 inches.

The apical end portion 18 is configured to be inserted into the cavity 26 to expand the porous member 14. Thus, in one form, an inner diameter d of the porous member 14 and defined by the cavity 26 may be slightly smaller than an outer diameter D of the rigid member 12. Since the modulus of elasticity of the porous member 14 is significantly less than the modulus of elasticity of the rigid member 12, urging the rigid member 12 apically into the cavity 26 will expand the porous member 14 generally radially outward and against the bone in the bore.

To place the implant 10 in a bore in bone, first, the practitioner uses a tool, which may be the same osteotome 24 or a separate tool, received in the cavity 26 to press the initially separate porous member 14 into the bore by applying a longitudinal force on the tool. Thus, the porous member 14 is placed in the bore before placing the rigid member 12 in the bore. Once the porous member 14 is in place, the practitioner uses the osteotome 24 to engage the rigid member 12 to create a longitudinal force and press or tap the rigid member 12 into the bore and subsequently into the cavity 26 of the porous member 14. As mentioned above, this action will expand the porous member 14 radially outward as well as compress the apical end portion 30 of the porous member 14 between the rigid member 12 and a bottom of the bore (similar to the bottom 64 of the bore 60 shown in FIG. 11). This forces the porous member 14 to cut into the adjacent bone defining the bore and create initial stability in multiple directions as described above. Once the apical end portion 18 is fully inserted into the cavity 26, the rigid member 12 forms a core for the porous member 14, and the porous member 14 at least generally covers the apical end portion 18.

In an alternative aspect, however, the rigid member 12 and the porous member 14 can be assembled together before insertion into the bore, and even preassembled by the manufacturer or supplier before the implant 10 is received by the practitioner. In this case, the porous member 14 is at least partially mounted on the apical end portion 18 of the rigid member 12 before the two members 12 and 14 are placed in a bore in bone. If the implant 10 is assembled first before it is inserted into the bore, the rigid member 12 may be driven into the porous member 14 a sufficient depth just to retain the porous member 14 on the rigid member 12 without significantly expanding the porous member 14. Once the implant 10 is placed into the bore, then the osteotome 24 can be pressed with a longitudinal force sufficient to expand the porous member 14 radially outward and into the bone.

As another option, the porous member 14 can be secured to the rigid member 12 by a loose press-fit that permits the porous member 14 to be separated from the rigid member 12 easily, such as by hand. In other words, the apical end portion 18 of the rigid member 12 is dimensioned to easily slip in and out of cavity 26. In this case, the diameters d and D of the cavity 26 and rigid member 12 are sufficiently close to form an interference fit that holds the members 12 and 14 together without significant expansion until the implant is inserted and assembled in the bore in the bone. Once inserted, significant force may be applied to the osteotome 24 in multiple directions to press the porous member 14 against the surrounding bone forming the bore.

While an interference fit between the rigid member 12 and porous member 14 is mentioned, it will be understood that adhesives, welding, and/or heat may be used to additionally or alternatively connect the two parts together, especially when the implant 10 is to be preassembled.

It will also be appreciated that the porous member 14 may alternatively extend over most, or substantially all, of the coronal-apical length of the implant 10, or the porous member 14 may only cover certain sections of the rigid member 12 instead of only cupping the apical end 18 of rigid member 12. Thus, it may be cylindrical, and the rigid member 12 may or may not extend all the way through the porous member 14 to form an apical end of the implant 10. Also, the apical end portion 30 of the porous member 14 may be provided in varying desired thicknesses (in the coronal-apical direction) to provide different porous lengths extending apically from the apical end portion 18 of the rigid member 12. Otherwise, the total assembled length of implant 10 may be provided in different desired dimensions by varying the length of rigid member 12.

Alternatively, a wide portion 32 (shown in dashed line on FIGS. 1-2) of the rigid member 12 may be provided to additionally engage a coronally facing, annular surface 34 of the porous member 14. Specifically, the wide portion 32 has a diameter larger than a diameter of the apical end portion 18 to form an apically facing, annular shoulder 38 extending radially outward from the apical end portion 18. The shoulder 38 engages the surface 34 when the rigid member 12 is pressed apically against the porous member 14. In this case, when the practitioner impacts the driving tool 24 longitudinally on the apical end portion or driving end 16 of the rigid member 12, the wall or sidewall 28 of the porous member 14 is compacted between the shoulder 38 of the rigid member 12 and the bottom of the bore (similar to bottom 64 shown in FIG. 11) in which it is disposed. This causes the sidewall 28 to bulge or expand radially outward to contact, and cut into, surrounding bone.

While the wide portion 32 is shown to extend to the coronal end portion 16 of the rigid member 12, it will be understood that instead, the wide portion 32 may extend coronally from shoulder 38 any coronal-apical distance along the length of the rigid member 12 that is sufficient to transfer adequate force to the porous member 14. In one example, the wide portion 32 is in the form of a relatively thin flange 36 (as shown in dashed line in FIG. 2).

Referring to FIG. 11, in another alternative basic form, an implant 50 has a rigid member 52 that engages a porous member 54 at least partially made of the porous material as described above and as with the implant 10. Here, however, the porous member 54 does not have a main cavity. Instead, the porous member 54 has a coronally facing surface 56 for engaging an apical end portion 58 of the rigid member 52. As with implant 10, either the members 52 and 54 are placed separately into the bore 60 as shown in FIG. 11, or the members 52 and 54 are assembled before insertion into a bore 60 in bone 62. In the former case, the porous member 54 is placed in the bore 60, and the rigid member 52 is then placed in the bore 60 and pressed or tapped in a longitudinal direction (as represented by arrow 'A' on FIG. 11) until the rigid member 52 engages the porous member 54 so that the porous member 54 is compacted between a bottom 64 of the bore 60 and the rigid member 52. This causes a sidewall 66 of the porous member 54 to bulge or expand radially outward to engage the surrounding bone. The porous member 54 also is pressed apically to cut into the bone on the bottom 64 of the bore 60.

If the members 52 and 54 are to be preassembled before insertion into the bore 60, the members 52 and 54 may be attached to each other by interlocking structure on the apical end portion 58 and surface 56 or by other ways such as fasteners, adhesives, welding, heat, and so forth. Otherwise, once the implant 50 is placed in the bore 60 the procedure is the same as if the members 52 and 54 were initially separate. Instead of being completely porous, porous member 54 may have a core of a different solid material or have its pores filled with a different material as described above as long as it does not significantly interfere with the required compression of the porous member 54 for its radial expansion.

Referring now to FIG. 8, as yet another alternative form, an implant 70 has a similar structure to implant 10 including a rigid member 72 and a porous member 74 with a longitudinal cavity 76 for receiving the rigid member 72. Except here, the rigid member 72, or at least an apical end portion 78 of the rigid member 72 that extends into cavity 76, and the porous member 74 have transverse cross sections that are non-circular. While other shapes are contemplated (such as polygonal, other shapes with flat sides, other irregular curved shapes, or combinations of the two), in the illustrated form, the cross sections of the apical end portion 78 and the porous member 74 are oval or elliptical. So configured, once the apical end portion 78 extends within the cavity 76 in a corresponding orientation as that of the porous member 74 (i.e., where the major axes of both cross sections extend generally in the same direction), the rigid member 72 may be rotated relative to the porous member 74, as illustrated by arrows X. The porous member 74 is sufficiently thin such that the rotation of the rigid member 72 causes the major diameter of the apical end portion 78 to be forced toward or into the minor diameter of the porous member 74, which causes the porous member 74 to bulge or expand radially outward (as shown by bulges 80) to engage the surrounding bone.

Referring to FIG. 9, an implant 90 has further alternative features that may also be applied to implant 10. The implant 90, as with implant 10, comprises a rigid member 92 and a porous member 94 with a cavity 96 for receiving an apical end portion 98 of the rigid member 92. Here, however, the apical end portion 98 can further include threads 91 for screwing the rigid member 92 into the cavity 96. The cavity 96 may or may not have a threaded portion 93 for engaging the threads 91. Whether or not the apical end portion 98 is threaded, the apical end portion 98 may be tapered such that the apical end portion 98 is sloped inward as it extends apically. The taper 95 helps to locate the apical end portion 98 in the cavity 96 and to expand the porous member 94 when the tapered apical end portion 98 has diameters that are larger than the inner diameter defining the cavity 96 as the taper 95 at the apical end portion 98 extends coronally. To expand the porous member 94 once placed in a bore in bone, the rigid member 92 is driven longitudinally and apically, albeit by rotating the rigid member 92, into the porous member 94 to expand the porous member 94 generally radially outward and onto the surrounding bone. In this case, a coronal cavity 97 on rigid member 92 may be non-circular to receive a rotational force from a driving tool.

Referring to FIG. 10, in another form, an implant 100 has three pieces instead of two. The implant 100 includes a first, coronal, shell or rigid member 102; a second, porous member 104 made of the same material as porous member 14; and a third, apical, core member 106 threaded to the shell member 102. The porous member 104 is cylindrical and is mounted around a core portion 108 of the core member 106. The porous member 104 is clamped between an annular ledge 110 extending radially outward from the core portion 108 on the core member 106 and an annular, apical end surface 112 formed by the shell member 102.

The core portion 108 is threaded and fits into an interiorly threaded bore 114 defined by the shell member 102 and that is apically accessible. The core portion 108 has a coronal-apical length sufficient to extend through the porous member 104 and protrude coronally from the porous member 104 to engage the threaded bore 114. The shell member 102 has a coronally accessible cavity 116 for receiving a driving tool for rotating the shell member 102 to thread the shell member 102 onto the core member 106. This rotation adjusts the shell member 102 and core member 106 toward each other to longitudinally compress the porous member 104 between the surface 112 and shoulder 110, causing the porous member 104 to bulge or expand radially outward, as indicated by arrows B, to engage the surrounding bone. The threaded bore 114 is sufficiently deep to accommodate the insertion length of the core portion 108.

Alternative configurations are apparent such as where the core portion is on the coronal member rather than the apical member, the porous member extends additionally or alternatively on other sections of the coronal-apical length of the implant 100, and/or the core member and shell member are attached to each by other than threads such as a press-fit or by fasteners.

Referring to FIGS. 4-7, in a different form, an implant 200 is similar to implant 10 in that it has a first, coronal, rigid or shell member 202 and a second, porous member 204 made of similar materials as that mentioned above for implant 10.

Here, however, shell member 202 forms an outer shell to cover at least a part of the second, porous member 204, and rather than being cup-shaped with an interior cavity, the porous member 204 is a relatively solid piece as with porous member 54 on implant 50. The porous member 204 is at least partially porous, but in the illustrated embodiment substantially porous, or alternatively may have a core of a different material or the porous material may be injected to form a core with a different filler material as mentioned previously.

The shell member 202 has a body 206 that defines a longitudinal or axial cavity 208 open at an apical or distal end portion 210 of the shell member 202. The porous member 204 is at least partially disposed within the longitudinal cavity 208 when assembled together, and in the illustrated form, extends apically from the shell member 202 to form the apical end 212 of the implant 200. The porous member 204 may also have a sidewall 214 that tapers inwardly as it extends coronally to assist with locating the porous member in cavity 208 and expanding radially outward when pressed to the shell member 202.

The longitudinal cavity 208 extends at least along the apical end portion 210 but may alternatively extend the entire length of the shell member 202 so that the longitudinal cavity 208 forms a coronally accessible hole 216 for receiving a driving tool 24 (FIG. 3). In this case, the interior surface 218 (shown in dashed line) defining the longitudinal cavity 208 has a jog or annular shoulder 220 to engage a coronal surface 222 of the porous member 204. With this configuration, the shell member 202 will engage the porous member 204 at the shoulder 220 to impact the porous member 204 as the shell member 202 is tapped or driven apically on the porous member 204. Otherwise, with the longitudinal cavity 208 open the entire length of the shell member 202, the driving tool may additionally or alternatively impact the porous member 204 directly as explained in greater detail below.

Alternatively, an interior wall 224 (shown in dashed line) divides the longitudinal cavity 208 from the coronal hole 216 that receives the driving tool. In this case, the apical surface 226 of the interior wall 224 engages the porous member 204.

The body 206 of the shell member 202 also has at least one opening 227 providing generally radial access to the longitudinal cavity 208 to permit the porous member 204 to extrude radially outward and through the openings to engage bone. In one form, the openings are generally longitudinally extending slots 228 extending along the apical end portion 210 to an apical end surface 230 of the shell member 202. In the illustrated form, a plurality of longitudinal slots 228 are uniformly spaced around the body 206. Here, six slots 228 are provided but any desired number of slots may be used. The height of the slots 228 may vary, either uniformly or from each other, and may extend at least a majority of the length of the body 206 or even substantially the entire length of the body 206 if desired. In the illustrated form, the porous member 204 extends longitudinally within longitudinal cavity 208 for a length at least sufficient to engage the entire length of the slots 228 as shown in FIG. 5.

In order to permit the porous member 204 to expand or extrude through the slots 228, or at least into the slots 228 and to the exterior of the shell member 202, the body 206 is made of a cylindrical wall 232 that defines the slots 228 and that has a thickness at least in the vicinity of the slots 228 of about 0.010 inches or less. So configured, the porous member 204 need only expand 0.010 inches or more to engage bone. The body 206 should not bend significantly if at all. In one form, the body 206 may be made of titanium and has a stiffness of about 110 GPa compared to the 3 GPa of the porous member 204 and as described above for porous member 14. Expanding or extruding the porous member 204 through the slots 228 will form an outwardly and radially extending porous rib 234 (as shown on FIG. 6) at each slot 228 for engaging surrounding bone. Each rib 234 generally runs longitudinally along the shell member 202 to correspond to the shape of the slot 228.

With the structure of implant 200 described, the porous member 204 can be separately placed in a bore in bone (such as the bore 60 shown in FIG. 11), and the shell member 202 is placed subsequently in the bore and onto the porous member 204. In another form, however, the porous member 204 is placed in the longitudinal cavity 208 before the implant 200 is placed in the bore in bone. In either case, the porous member 204 may be secured within the longitudinal cavity 208 by an interference fit, or alternatively, the porous member 204 merely initially has a loose press-fit within the longitudinal cavity 208. In the latter case, and when the porous member 204 is provided in different coronal-apical lengths, for example, the practitioner can replace the porous member 204 from the shell member 202 until a porous member 204 of an adequate coronal-apical length is selected.

Once the porous member 204 is mounted on the shell member 202, the osteotome 24 or other driving tool is mounted on the driving end of the shell member 202 or more specifically, in the coronal hole 216 on the shell member 202 to place the implant 200 within the bore in the bone (such as that shown in FIG. 11). As the osteotome 24 is driven or tapped in an insertion direction, the osteotome 24 engages the interior wall 224, if present, and/or a coronal end surface 236 of the shell member 202. It will be understood that the interior surface 218 of the shell member 202 may also have shoulders or ledges to receive the driving member or osteotome 24 for driving the shell member 202 apically.

Once the porous member 204 is seated on a bottom of the bore in the bone, further impacting the driving tool on the driving end of the shell member 202 with a longitudinal force compacts the porous member 204 between the shell member 202 and the bottom of the bore. This, in turn, causes the sidewall 214 of the porous member 204 to expand radially outward and extrude into or through the slots 228 to form the ribs 234 to engage surrounding bone (as shown in FIG. 6).

For the alternative configuration where the longitudinal cavity 208 extends the length of the shell member 202 and the interior wall 224 is not present, the driving tool 24 may directly engage the driving end or coronal surface 222 of the porous member 204. In this case, the driving tool engages the coronal end surface 236 of the shell member 202, engages a shelf or shoulder on the interior surface 218, or has an interference fit with the interior surface 218 for initial placement of the implant 200 in the bore in bone. Once so disposed, further impact of the driving tool on the driving end (or in this case, the porous member 204) compacts the porous member 204 between the driving tool and the bottom of the bore. This expands the sidewall 214 of the porous member 204 radially outward and into or through the slots 228 to form the ribs 234.

The expanded porous ribs 234 cut into the bone as described above and anchors the implant 200 in the bore in which it is disposed to provide stable initial stability to receive immediate mastication forces. Since the ribs 234 extend into the cortical bone, such configuration provides the implant 200 an additional torsional stability. The porous nature of the material forming the ribs 234 also aids in enhancing the speed of osseointegration of the implant 200 with the bone as described above.

The above described press-fit dental implants may be conventionally machined or cut using Electrical Discharge Machining (EDM). The above described press-fit dental implants may also be made by using the net-shape manufacturing process as owned by Zimmer Trabecular Metal Technologies, Inc.

While this invention may have been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone implant comprising:
   a coronal member formed of a relatively rigid coronal member material and defining an apical end surface;
   an apical member formed of a relatively rigid apical member material and defining a ledge, the apical member configured to adjustably engage the coronal member to define a space between the apical end surface and the ledge; and
   a porous member formed of a relatively flexible porous member material that is at least partially porous, the porous member being removably positionable between the apical end surface of the coronal member and the ledge of the apical member, such that adjusting the coronal member and the apical member toward each other longitudinally compresses the porous member and expands the porous member generally radially outward.

2. The bone implant of claim 1, in which the coronal member is configured to threadably engage the apical member.

3. The bone implant of claim 1, in which the coronal member comprises a smooth exterior surface.

4. The bone implant of claim 1, in which the apical member comprises a smooth exterior surface.

5. The bone implant of claim 1, in which the porous member material comprises a porous metal.

6. The bone implant of claim 1, in which the porous member material comprises tantalum.

7. The bone implant of claim 1, in which at least one of the coronal member and the apical member includes a core, and in which the porous member has a cylindrical profile defining a longitudinal cavity configured to receive the core.

8. The bone implant of claim 1, in which the porous member material has a compressive strength in a range of approximately 50 to 90 MPa.

9. The bone implant of claim 1, in which the porous member material has a stiffness of approximately 3 Gpa or less.

10. The bone implant of claim 1, in which the coronal member further includes a coronally accessible cavity configured to receive a portion of a driving tool.

11. The bone implant of claim 1, in which the porous member comprises a generally cylindrical wall having a thickness of approximately 0.020 to 0.040 inches.

12. A dental bone implant for use with a bore formed in a dentition site, the dental bone implant comprising:
    a coronal member formed of a relatively rigid coronal member material, the coronal member including an apical end surface;
    an apical member formed of a relatively rigid apical member material and defining a ledge, wherein a space is defined between the apical end surface of the coronal member and the ledge of the apical member;
    a core extending between the coronal member and the apical member, the core being configured to adjustably engage at least one of the coronal member and the apical member; and
    a porous member formed of a relatively flexible porous member material that is at least partially porous, the porous member having a generally hollow, cylindrical shape configured to receive the core, the porous member being disposed in the space between the apical end surface of the coronal member and the ledge of the apical member;
    wherein the core is adjustable along a longitudinal direction to longitudinally compress the porous member to expand the porous member generally radially outward and decrease an overall longitudinal length of the implant.

13. The dental bone implant of claim 12, in which the coronal member includes an apically accessible bore, and the core is configured to adjustably engage the apically accessible bore.

14. The dental bone implant of claim 13, in which the core and the apically accessible bore comprise complementary threads.

15. The dental bone implant of claim 12, in which the core has a non-circular outer surface, and in which rotation of the core causes the porous member to expand radially outward.

16. The dental bone implant of claim 12, in which the core has a coronal portion with an outer diameter larger than an inner diameter of the porous material, in which the core tapers inwardly as it extends apically, and in which the core is adjustable in the longitudinal direction so that the coronal portion of the core expands the porous member generally radially outward.

17. The dental bone implant of claim 12, in which the coronal member comprises a smooth exterior surface.

18. The dental bone implant of claim 12, in which the apical member comprises a smooth exterior surface.

19. The dental bone implant of claim 12, in which the porous member material comprises a porous metal.

20. The dental bone implant of claim 12, in which the porous member material comprises tantalum.

21. The dental bone implant of claim 12, in which the coronal member further includes a coronally accessible cavity sized to receive a portion of a driving tool.

22. The dental bone implant of claim 12, in which the porous member comprises a wall having a thickness of approximately 0.020 to 0.040 inches.

23. A bone implant comprising:
    a coronal member formed of a relatively rigid coronal member material and defining an apical end surface, the coronal member including an apically accessible bore;
    an apical member formed of a relatively rigid apical member material and defining a ledge, the apical member configured to adjustably engage the coronal member to define a space between the apical end surface and the ledge, the apical member including a core configured to be apically received by the bore so as to define a core receiving zone disposed between the core and the coronal member; and
    a porous member formed of a relatively flexible porous member material that is at least partially porous, the porous member being disposed between the apical end surface of the coronal member and the ledge of the apical member, wherein adjusting the coronal member and the apical member toward each other longitudinally compresses the porous member and expands the porous member generally radially outward, wherein the porous member has a cylindrical profile defining a longitudinal cavity configured to receive the core.

24. The dental bone implant of claim 23, in which the core is adjustable in a longitudinal direction to longitudinally compress the porous member, thereby to expand the porous member generally radially outward; and the core is configured to adjustably engage the apically accessible bore, in which the core and the apically accessible bore comprise complementary threads.

25. The dental bone implant of claim 23, in which the core has a non-circular outer surface, and in which rotation of the core causes the porous member to expand radially outward.

26. The dental bone implant of claim 23, in which the core has a coronal portion with an outer diameter larger than an inner diameter of the porous material, in which the core tapers inwardly as it extends apically, and in which the core is adjustable in a longitudinal direction so that the coronal portion of the core expands the porous member generally radially outward.

27. The dental bone implant of claim 23, in which the coronal member further includes a coronally accessible cavity sized to receive a portion of a driving tool.

* * * * *